United States Patent
Linares et al.

(10) Patent No.: US 9,114,015 B2
(45) Date of Patent: Aug. 25, 2015

(54) IMPLANTABLE ELBOW JOINT ASSEMBLY WITH SPHERICAL INTER-SUPPORT

(71) Applicant: Linares Medical Devices, LLC, Auburn Hills, MI (US)

(72) Inventors: Miguel A. Linares, Bloomfield Hills, MI (US); Miguel A. Linares, Jr., Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 0 days.

(21) Appl. No.: 14/454,276

(22) Filed: Aug. 7, 2014

(65) Prior Publication Data

US 2014/0350684 A1 Nov. 27, 2014

Related U.S. Application Data

(62) Division of application No. 13/624,403, filed on Sep. 21, 2012, now Pat. No. 8,840,673.

(60) Provisional application No. 61/537,123, filed on Sep. 21, 2011.

(51) Int. Cl.
*A61F 2/38* (2006.01)
*A61F 2/30* (2006.01)

(52) U.S. Cl.
CPC ........ *A61F 2/3804* (2013.01); *A61F 2002/3021* (2013.01); *A61F 2002/3064* (2013.01); *A61F 2002/30637* (2013.01); *A61F 2002/30642* (2013.01); *A61F 2002/30644* (2013.01); *A61F 2002/30649* (2013.01); *A61F 2002/30652* (2013.01); *A61F 2002/30878* (2013.01); *A61F 2002/30892* (2013.01); *A61F 2002/3809* (2013.01); *A61F 2002/3813* (2013.01); *A61F 2310/00011* (2013.01)

(58) Field of Classification Search
CPC ........ A61F 2/3804; A61F 2/38; A61F 2/4605
USPC ............................................. 623/20.11–20.13
See application file for complete search history.

(56) References Cited

U.S. PATENT DOCUMENTS

| 807,473 A | 12/1905 | Kolar et al. |
| 3,547,115 A * | 12/1970 | Stevens ...................... 606/86 R |
| 3,638,243 A | 2/1972 | Campbell, Jr. et al. |
| 3,694,821 A | 10/1972 | Moritz |
| 3,696,446 A | 10/1972 | Bousquet et al. |
| 3,772,709 A * | 11/1973 | Swanson .................... 623/20.12 |

(Continued)

FOREIGN PATENT DOCUMENTS

GB 2468967 A 9/2010

*Primary Examiner* — Alvin Stewart
(74) *Attorney, Agent, or Firm* — Gifford, Krass, Sprinkle, Anderson & Citkowski, P.C.; Douglas J. McEvoy

(57) ABSTRACT

A multi-component elbow joint assembly incorporated into reconditioned end surfaces established between an upper humerus bone and opposing lower radius and ulna bones. The assembly includes a first component anchored into the upper humerus reconditioned end surface and exhibits a first exposed support surface. A second component is anchored into the lower reconditioned bone end surface of at least one of the radius and ulna bones and exhibits a second exposed support surface. An intermediate component is supported in at least one of eccentric or rotational fashion between the first and second anchored components.

15 Claims, 3 Drawing Sheets

(56) References Cited

U.S. PATENT DOCUMENTS

| | | | |
|---|---|---|---|
| 3,795,922 A | 3/1974 | Herbert et al. | |
| 3,837,008 A | 9/1974 | Bahler et al. | |
| 3,868,730 A | 3/1975 | Kaufer et al. | |
| 3,886,601 A | 6/1975 | Findlay | |
| 3,909,853 A | 10/1975 | Lennox | |
| 3,916,451 A | 11/1975 | Buechel et al. | |
| 3,919,725 A | 11/1975 | Swanson et al. | |
| 3,987,500 A | 10/1976 | Schlein | |
| 3,992,726 A | 11/1976 | Freeman et al. | |
| 4,003,095 A | 1/1977 | Gristina | |
| 4,008,495 A * | 2/1977 | Cavendish et al. | 623/20.11 |
| 4,024,588 A * | 5/1977 | Janssen et al. | 623/18.12 |
| 4,038,704 A * | 8/1977 | Ring | 623/20.11 |
| 4,040,130 A | 8/1977 | Laure | |
| 4,057,858 A * | 11/1977 | Helfet | 623/20.11 |
| 4,079,469 A * | 3/1978 | Wadsworth | 623/20.12 |
| 4,106,128 A | 8/1978 | Greenwald et al. | |
| RE29,757 E * | 9/1978 | Helfet | 623/20.31 |
| 4,180,871 A | 1/1980 | Hamas | |
| 4,206,517 A | 6/1980 | Pappas et al. | |
| 4,224,695 A * | 9/1980 | Grundei et al. | 623/20.12 |
| 4,242,758 A * | 1/1981 | Amis et al. | 623/20.11 |
| 4,257,128 A | 3/1981 | Scales et al. | |
| 4,279,041 A | 7/1981 | Buchholz | |
| 4,293,963 A | 10/1981 | Gold et al. | |
| 4,378,607 A | 4/1983 | Wadsworth | |
| 4,383,337 A * | 5/1983 | Volz et al. | 623/20.12 |
| 4,538,306 A * | 9/1985 | Dorre et al. | 623/20.13 |
| 4,822,364 A * | 4/1989 | Inglis et al. | 623/20.12 |
| 4,846,840 A | 7/1989 | Leclercq et al. | |
| 4,936,848 A | 6/1990 | Bagby | |
| 4,950,299 A | 8/1990 | Noiles | |
| 5,314,485 A | 5/1994 | Judet | |
| 5,507,821 A | 4/1996 | Sennwald et al. | |
| 5,702,471 A | 12/1997 | Grundei et al. | |
| 5,723,018 A | 3/1998 | Cyprien et al. | |
| 5,782,923 A * | 7/1998 | Engelbrecht et al. | 623/20.13 |
| 5,879,395 A * | 3/1999 | Tornier et al. | 623/20.13 |
| 6,027,534 A * | 2/2000 | Wack et al. | 623/20.12 |
| 6,051,751 A | 4/2000 | Sioshansi et al. | |
| 6,117,175 A | 9/2000 | Bosredon | |
| 6,290,725 B1 * | 9/2001 | Weiss et al. | 623/20.12 |
| 6,290,726 B1 * | 9/2001 | Pope et al. | 623/22.15 |
| 6,306,171 B1 | 10/2001 | Conzemius | |
| 6,379,387 B1 * | 4/2002 | Tornier | 623/20.12 |
| 6,454,808 B1 | 9/2002 | Masada | |
| 6,579,321 B1 | 6/2003 | Gordon et al. | |
| 6,682,562 B2 | 1/2004 | Viart et al. | |
| 6,682,565 B1 | 1/2004 | Krishnan | |
| 6,689,169 B2 | 2/2004 | Harris | |
| 6,699,290 B1 | 3/2004 | Wack et al. | |
| 6,890,357 B2 | 5/2005 | Tornier | |
| 7,108,720 B2 | 9/2006 | Hanes | |
| 7,160,329 B2 | 1/2007 | Cooney, III et al. | |
| 7,195,644 B2 | 3/2007 | Diaz et al. | |
| 7,247,170 B2 | 7/2007 | Graham et al. | |
| 7,297,165 B1 * | 11/2007 | Kriek | 623/20.21 |
| 7,335,231 B2 | 2/2008 | McLean | |
| 7,393,362 B2 | 7/2008 | Cruchet et al. | |
| 7,419,507 B2 | 9/2008 | Cook et al. | |
| 7,468,076 B2 | 12/2008 | Zubok et al. | |
| 7,556,763 B2 | 7/2009 | Pope et al. | |
| 7,566,346 B2 | 7/2009 | Kirschman | |
| 7,708,781 B2 | 5/2010 | Scheker | |
| 7,780,737 B2 | 8/2010 | Bonnard et al. | |
| 7,837,738 B2 | 11/2010 | Reigstad et al. | |
| 7,959,678 B2 | 6/2011 | Filippi et al. | |
| 8,016,889 B2 | 9/2011 | Dixon et al. | |
| 8,070,823 B2 | 12/2011 | Kellar et al. | |
| 8,211,175 B2 | 7/2012 | Eisermann et al. | |
| 8,292,966 B2 | 10/2012 | Morton | |
| 8,333,806 B2 | 12/2012 | Scheker | |
| 8,377,066 B2 | 2/2013 | Katrana et al. | |
| 8,449,620 B2 | 5/2013 | Hakansson et al. | |
| 8,454,703 B2 | 6/2013 | Linares | |
| 8,545,566 B2 | 10/2013 | Niemiec et al. | |
| 8,545,571 B2 | 10/2013 | Collazo et al. | |
| 8,702,800 B2 | 4/2014 | Linares et al. | |
| 8,702,802 B2 | 4/2014 | Linares et al. | |
| 8,926,705 B2 * | 1/2015 | Linares et al. | 623/18.12 |
| 2001/0025199 A1 | 9/2001 | Rauscher | |
| 2002/0055785 A1 | 5/2002 | Harris | |
| 2002/0111690 A1 | 8/2002 | Hyde | |
| 2002/0143402 A1 | 10/2002 | Steinberg | |
| 2003/0009171 A1 * | 1/2003 | Tornier | 606/96 |
| 2003/0040805 A1 | 2/2003 | Minamikawa | |
| 2003/0204261 A1 | 10/2003 | Eisermann et al. | |
| 2003/0208276 A1 * | 11/2003 | Berelsman et al. | 623/20.11 |
| 2003/0208277 A1 | 11/2003 | Weiss et al. | |
| 2003/0208280 A1 | 11/2003 | Tohidi | |
| 2004/0059429 A1 | 3/2004 | Amin et al. | |
| 2004/0102853 A1 | 5/2004 | Boumann et al. | |
| 2004/0122524 A1 | 6/2004 | Hunter et al. | |
| 2004/0220675 A1 * | 11/2004 | Lewis et al. | 623/20.11 |
| 2004/0225370 A1 | 11/2004 | Cruchet et al. | |
| 2004/0243243 A1 * | 12/2004 | Tornier | 623/20.12 |
| 2005/0043806 A1 * | 2/2005 | Cook et al. | 623/20.12 |
| 2005/0149199 A1 | 7/2005 | Steinberg | |
| 2005/0158200 A1 | 7/2005 | Pope et al. | |
| 2005/0165490 A1 | 7/2005 | Tornier | |
| 2005/0177244 A1 | 8/2005 | Steinberg | |
| 2005/0246022 A1 | 11/2005 | Zubok et al. | |
| 2006/0004462 A1 | 1/2006 | Gupta | |
| 2006/0030946 A1 | 2/2006 | Ball et al. | |
| 2006/0095132 A1 | 5/2006 | Kirschman | |
| 2006/0100712 A1 * | 5/2006 | Ball | 623/20.13 |
| 2006/0111789 A1 * | 5/2006 | Ball | 623/20.13 |
| 2006/0142862 A1 | 6/2006 | Diaz et al. | |
| 2006/0173546 A1 | 8/2006 | Berelsman et al. | |
| 2006/0224243 A1 * | 10/2006 | Pare et al. | 623/20.11 |
| 2006/0235414 A1 | 10/2006 | Lim et al. | |
| 2006/0247786 A1 * | 11/2006 | Ball | 623/20.13 |
| 2007/0051180 A1 * | 3/2007 | White | 73/760 |
| 2008/0051909 A1 | 2/2008 | Wolfe et al. | |
| 2008/0195217 A1 * | 8/2008 | Scheker | 623/20.11 |
| 2008/0215156 A1 | 9/2008 | Duggal et al. | |
| 2009/0024221 A1 | 1/2009 | Ball | |
| 2009/0281631 A1 | 11/2009 | Naidu | |
| 2009/0287309 A1 | 11/2009 | Walch et al. | |
| 2009/0292364 A1 | 11/2009 | Linares | |
| 2009/0306781 A1 | 12/2009 | Kyomoto et al. | |
| 2009/0312840 A1 * | 12/2009 | Morrey | 623/20.11 |
| 2010/0017966 A1 | 1/2010 | Cho | |
| 2010/0087928 A1 | 4/2010 | Graham et al. | |
| 2010/0145465 A1 * | 6/2010 | Smirthwaite et al. | 623/20.12 |
| 2010/0179661 A1 * | 7/2010 | Berelsman et al. | 623/20.12 |
| 2010/0222887 A1 * | 9/2010 | Katrana et al. | 623/20.11 |
| 2010/0256770 A1 | 10/2010 | Hakansson et al. | |
| 2011/0035012 A1 | 2/2011 | Linares | |
| 2011/0035016 A1 | 2/2011 | Orbay et al. | |
| 2011/0098822 A1 | 4/2011 | Walch et al. | |
| 2011/0106271 A1 | 5/2011 | Regala et al. | |
| 2011/0125274 A1 * | 5/2011 | Bartel et al. | 623/20.11 |
| 2011/0172781 A1 * | 7/2011 | Katrana et al. | 623/20.11 |
| 2011/0238185 A1 | 9/2011 | Filippi et al. | |
| 2012/0053697 A1 * | 3/2012 | Palmer et al. | 623/20.12 |
| 2012/0136450 A1 | 5/2012 | Wendelburg et al. | |
| 2012/0221113 A1 * | 8/2012 | Katrana et al. | 623/20.12 |
| 2013/0013069 A1 | 1/2013 | de Villiers et al. | |
| 2013/0030537 A1 * | 1/2013 | Linares et al. | 623/18.11 |
| 2013/0053969 A1 | 2/2013 | Linares et al. | |
| 2013/0053972 A1 | 2/2013 | Linares et al. | |
| 2013/0079886 A1 | 3/2013 | Linares et al. | |
| 2013/0090738 A1 | 4/2013 | Linares et al. | |
| 2013/0090739 A1 | 4/2013 | Linares et al. | |
| 2013/0090740 A1 | 4/2013 | Linares et al. | |
| 2013/0103158 A1 * | 4/2013 | Linares et al. | 623/20.11 |
| 2013/0345818 A1 * | 12/2013 | Wagner et al. | 623/20.12 |
| 2014/0025174 A1 * | 1/2014 | Lucas et al. | 623/20.24 |
| 2014/0121779 A1 * | 5/2014 | Gonzalez-Hernandez | 623/20.12 |
| 2014/0277525 A1 * | 9/2014 | Winslow | 623/20.12 |

\* cited by examiner

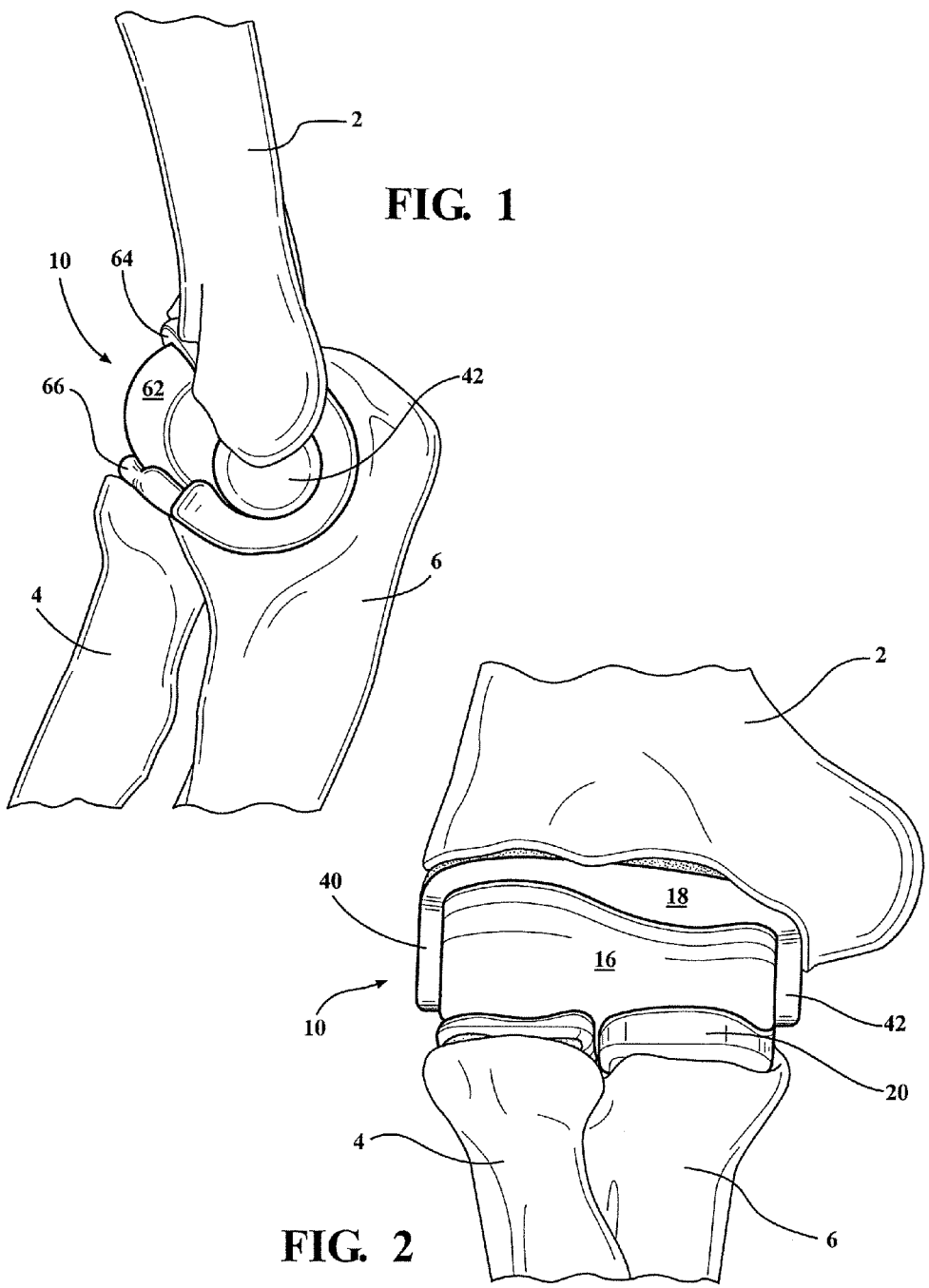

IMPLANTABLE ELBOW JOINT ASSEMBLY WITH SPHERICAL INTER-SUPPORT

CROSS-REFERENCE TO RELATED APPLICATIONS

This application is a Division of application Ser. No. 13/624,403 filed on Sep. 21, 2012. Application Ser. No. 13/624,403 claims the benefit of U.S. Provisional Application 61/537,123 filed on Sep. 21, 2011, the contents of which are incorporated herein in their entirety.

FIELD OF THE INVENTION

The present invention discloses an artificial joint assembly, such as is particularly configured for employing as a retrofit elbow joint, and which combines multiple artificial components incorporated into first and second reconditioned joint defining surfaces for providing increased wear life in tandem with evenly distributed wear pattern/profile as well as enhanced flexibility and mobility.

BACKGROUND OF THE INVENTION

The prior art is documented with examples of artificial implant assemblies. Among these are included the artificial elbow joint of Ikegami U.S. Pat. No. 8,100,980 which teaches a humeral component made of metal and an ulnar component made of resins for replacing an elbow joint. The humeral component is configured by a substantially cylindrical trochlea and a stem extending from the trochlea that is inserted into the humeral. An ulnar component is configured by a joint surface member which receives the trochlea in a rotatable manner and a stem which extends from the joint surface member and is inserted into the ulna. The stem of the humeral component is curved gently downward overall so as to comply with the lordotic shape of the humeral, and the trachea is turnable about the centerline of the stem.

A further example of a minimally thick orthopedic prosthesis which closely matches a minimally reshaped joint defining bone surface by an orbital or lineally oscillating orthopedic resurfacing tool in the minimally invasive orthopedic surgical repair or reconstruction of a variety of joints.

SUMMARY OF THE INVENTION

The present invention discloses a multi-component elbow joint assembly incorporated into reconditioned end surfaces established between an upper humerus bone and opposing lower radius and ulna bones. The assembly includes a first component anchored into the upper humerus reconditioned end surface and exhibits a first exposed support surface. A second component is anchored into the lower reconditioned bone end surface of at least one of the radius and ulna bones and exhibits a second exposed support surface.

An intermediate component is supported in at least one of eccentric or rotational fashion between the first and second anchored components. The intermediate component further exhibits an uneven roller shape.

Each of the anchored components further exhibits a concave surface for supporting the intermediate component. The anchored components may also include a widened uneven surface for supporting a corresponding uneven profile associated with the intermediate positioned roller. Each of the first, second and intermediate components may be constructed from any of metal, plastic, polymer or composite material. Additional features include a plurality of surface projecting bearings mounted within the intermediate positioned and uneven surfaced roller component for facilitating a rotational interface established therebetween.

BRIEF DESCRIPTION OF THE DRAWINGS

Reference will now be made to the attached drawings, when read in combination with the following detailed description, wherein like reference numerals refer to like parts throughout the several views, and in which:

FIG. 1 is a side perspective of an elbow implant assembly according to the present invention;

FIG. 2 is a rotated front plan view of the elbow implant assembly of FIG. 1 and better depicting the roller shape associated with the intermediate support element;

DETAILED DESCRIPTION OF THE PREFERRED EMBODIMENTS

As will be disclosed with succeeding reference to the several depicted embodiments, the present invention discloses an artificial joint assembly, such as is particularly configured for employing as a retrofit elbow joint, and which combines multiple artificial components incorporated into first and second reconditioned joint defining surfaces for providing increased wear life in tandem with evenly distributed wear pattern/profile as well as enhanced flexibility and mobility.

The joint assemblies described herein are particularly configured for such as in situ reconditioned installation within a patient's elbow (between the lower end of the upper humerus bone and corresponding upper ends of the lower radius and ulna bones), however it is further understood that certain applications could in theory include other joint applications, either human or other mammalian. For purposes of ease and clarify of illustration, the various embodiments depicted further do not include reference to additional necessary components of the elbow joint, such as including associated muscles, tendons and ligaments, the inclusion of which are assumed and which collectively define a functioning and articulating elbow.

Figure 3:
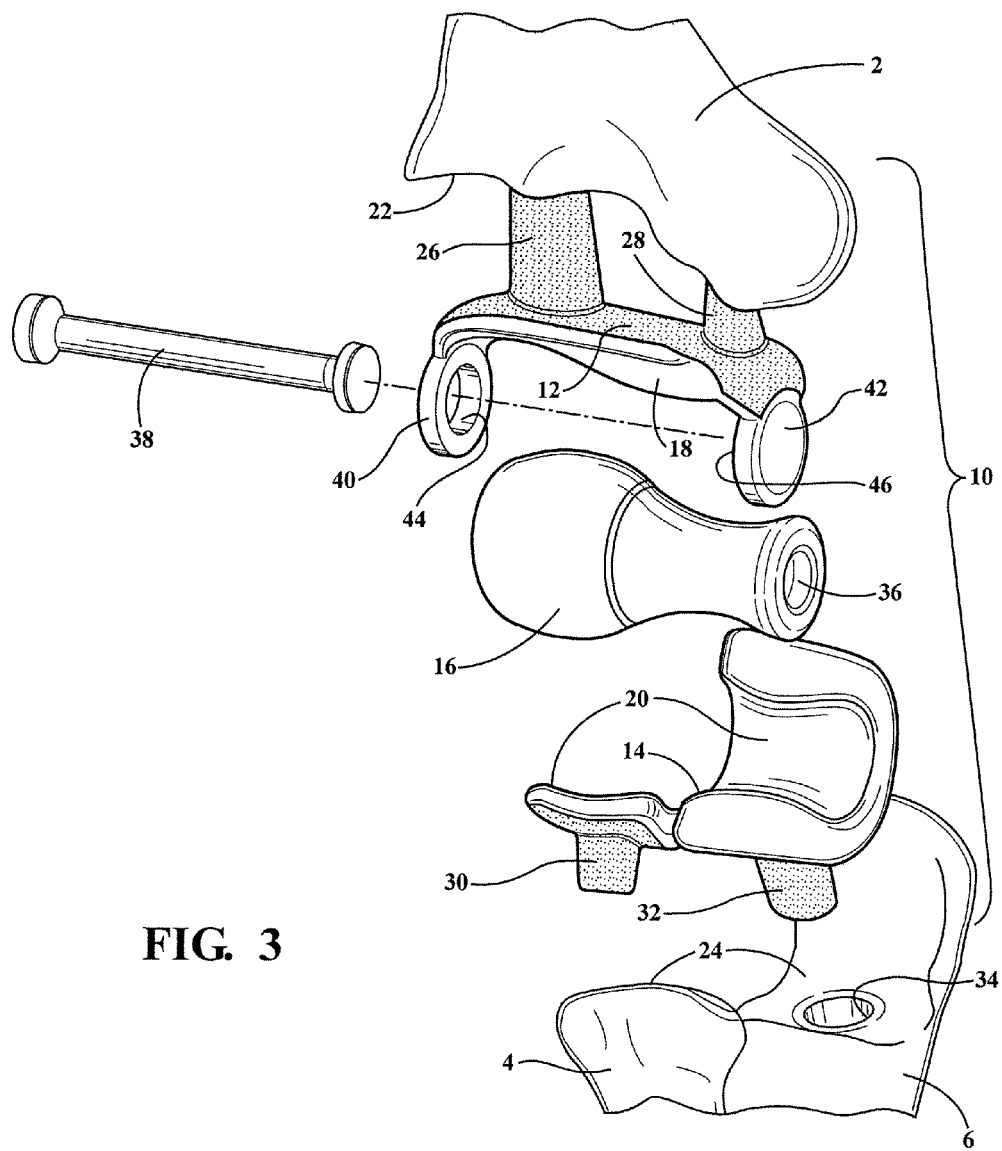
FIG. 3 is an exploded view of the elbow implant assembly of FIGS. 1 and 2 and better illustrating the reconditioned end-configurations established between the upper humerus and lower radius and ulna arm bones, combined with the configuration of the implant support inserts and intermediate positioned and pseudo bowling pin shape associated with the intermediate positioned roller support.

Referring now to FIGS. 1-3 in succession, a series of side perspective, front plan and exploded views are depicted of an elbow implant assembly 10 and which combines an arrangement of end surface attachable implant portions 12 and 14 in combination with an interposed and substantially irregular (e.g. vase like or pseudo bowling pin) shaped roller 16 which seats within concave widened surface profiles 18 and 20 associated with exposed seating locations of the implant portions 12 and 14. Both an upper humerus 2 and lower radius 4/ulna 6 joint surfaces are provided and include reconditioned ends, such as shown by profiles 22 and 24, respectively in FIG. 3, and such that the widened implants 12 and 14 are seated in end-anchoring fashion in the manner best depicted in the frontal view of FIG. 2.

As again shown in the exploded view of FIG. 3, the implants 12 and 14 each again include reverse side extending (pairs) of stems (see at 26 and 28 for upper implant 12 and further at 30 and 32 for lower implant 14) for respectively seating within aligning recessed apertures (exemplified at 34 for ulna bone 6) defined in each of the reconditioned elbow joint end faces. Roughened undercut patterns are exhibited on the reverse adhering faces of the implants 12 and 14 and promote long term bone in-growth to permanently anchor the implants in place.

The width extending and irregular surfaces 18 and 20 associated with the implants 12 and 14 exhibit a combination of both concave and uneven profiles (again FIG. 3) such that the irregular shaped (bowling pin like) roller 16 seats in a mating rotatable fashion therebetween as best depicted in the frontal plan view of FIG. 2. As again best shown in FIG. 3, a central aperture 36 extends longitudinally through an interior of the roller 16 and is engaged by a pin shaft 38 upon pre-positioning the roller 16 between a pair of downward extending end lobes 40 and 42 associated with the upper implant 18, the first end lobe 40 including an inner aperture 44 for permitting initial insertion of the pin shaft 38, with the opposite end located lobe 42 exhibiting an abutting inner end face 46 defining an end stop of the inserting pin shaft 38 and thereby mounting the pseudo bowling pin shaped roller 16 in a supported and rotatable fashion.

As is known, a suitable arrangement of ligaments, tendons and muscles can be employed for retaining the arrangement of the elbow joint 10 and such as which can be (to the extent possible) retained from the original joint construction of the patient and which can be avoided to the extent possible during in situ end face reconditioning and implantation of the joint assembly. As also previously described, the material construction of the various components 12, 14 and 16 can include an arrangement in which either a plastic/composite or metal can be employed in each of the outer implant portions 12 and 14, with the alternating material employed in the construction of the pseudo roller pin shaped element 16.

Figure 4:
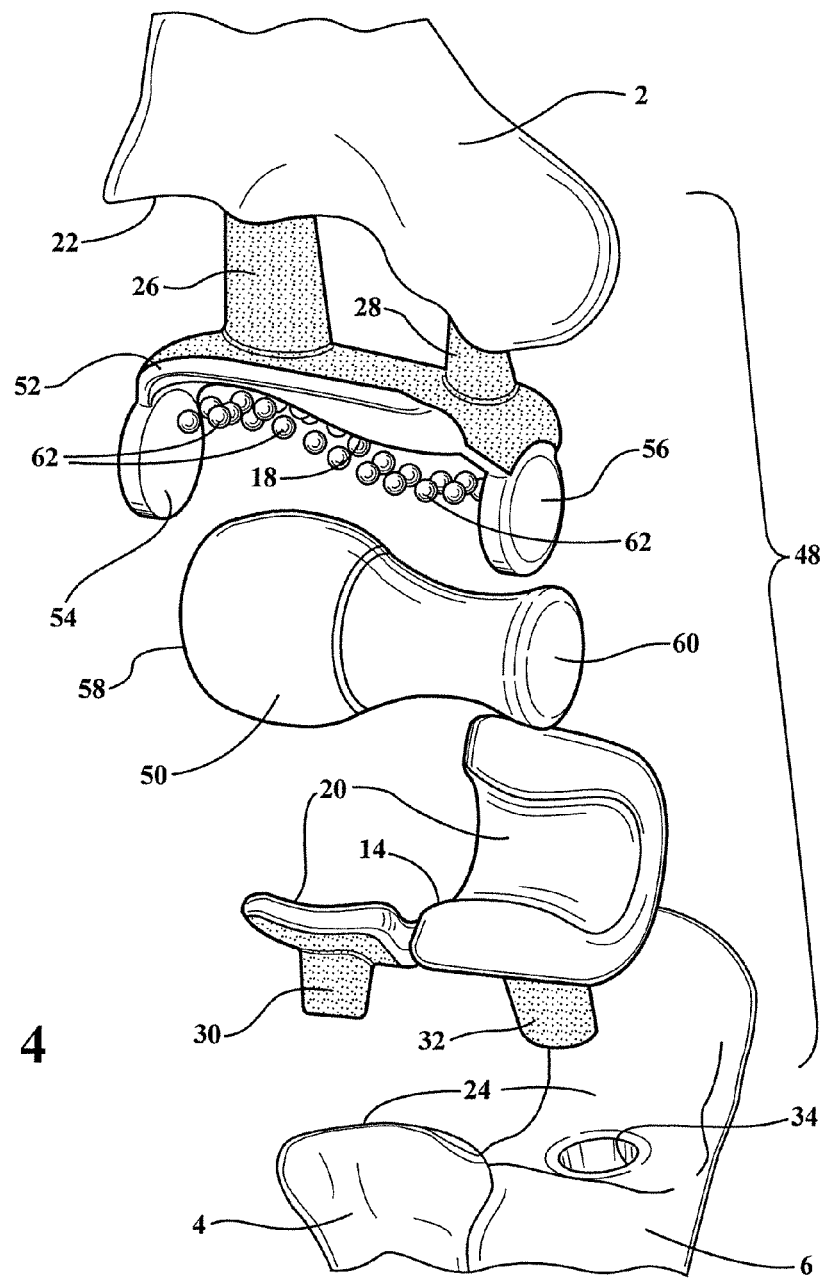
FIG. 4 is a further exploded view similar to as shown in FIG. 3 of a slightly modified variant of roller pin supporting elbow implant assembly and which depicts in further exploded fashion a plurality of ball bearings substantially integrated into the anchored implant associated with the reconditioned end face of the humerus and which provide additional rotational support to the intermediate roller.

Referring now to FIG. 4, a further exploded view similar to as shown in FIG. 3 is presented generally at 48 of a slightly modified variant of roller pin supporting elbow implant assembly and in which the only appreciable differences from FIG. 3 include the provision of a roller pin/uneven shaped roller 50 as a solid component (without internal aperture 36 as in FIG. 3) combined with a reconfigured upper implant 52 with solid end lobes 54 and 56 for snap fitting therebetween each of opposite end surfaces 58 and 60 associated with the uneven roller 50. Although not clearly shown, it is envisioned that the inner facing surfaces of the lobes 54 and 56 can each exhibit one of either a convex or concave shape with alternates with that exhibited by the outer facing end surfaces 58 and 60 of the roller 50, and so as to maintain the roller 50 without the need of the lateral mounting pin shaft 38 of FIG. 3. The implants 52 and 14 otherwise retain the features of the reverse extending mounting stems 26/28 and 30/32 along with the roughened/undercut bone in-growth promoting reverse surfaces.

Also depicted in FIG. 4 in further exploded fashion are a plurality of, generally micro sized, ball bearings 62. Although not clearly providing an underside view of the concave/irregular pin supporting surface associated with the underside of the implant 52, the bearings 62 are substantially seated in distributed fashion along the humerus end face anchored implant 52 (this defined as being substantially embedded within the concave/irregular support face previously identified at 18 in FIG. 3 of the upper corresponding implant 58), and which provides additional rotational support to the intermediate roller 50.

Having described my invention, other and additional preferred embodiments will become apparent to those skilled in the art to which it pertains, and without deviating from the scope of the appended claims.

We claim:

1. A multi-component elbow joint assembly incorporated into reconditioned end surfaces established between an upper humerus bone and opposing lower radius and ulna bones, said assembly comprising:
   a first component anchored into the upper humerus reconditioned end surface and exhibiting a first support surface;
   a second component anchored into the lower reconditioned bone end surface of at least one of the radius and ulna bones and exhibiting a second exposed support surface;
   an elongated and uneven roller shaped intermediate component supported in rotational fashion between said first and second anchored components; and
   each of said anchored components further exhibiting a concave surface for supporting therebetween said intermediate component, said anchored components each further having a widened uneven surface for supporting a corresponding uneven profile associated with said intermediate positioned roller shaped component.

2. The joint assembly as described in claim 1, each of said first, second and intermediate components further being constructed of at least one of a metal, plastic, polymer or composite material.

3. The joint assembly as described in claim 1, further comprising a plurality of ball bearings seated in distributed fashion along said concave surface of at least one of said anchored implants for providing rotational support to said roller shaped intermediate component.

4. The joint assembly as described in claim 1, further comprising a central aperture extending longitudinally through an interior of said uneven roller shaped intermediate component which is engaged by a pin shaft upon pre-positioning said intermediate component between a pair of downward extending end lobes associated with said first component, a first of said end lobes including an inner aperture for permitting initial insertion of said shaft, with an opposite end located and other of said lobes exhibiting an abutting inner end face defining an end stop of said inserting shaft, thereby mounting said roller in a stationary rotatable position.

5. The joint assembly as described in claim 4, further comprising a plurality of micro sized ball bearings seated in distributed fashion along an end face of said first component in substantially embedded and eccentrically rotatable fashion within a concave/irregular support face of said first component, said bearings providing additional rotational support to said intermediate positioned roller.

6. The joint assembly as described in claim 1, each of said anchored components further exhibiting a concave surface for supporting therebetween said intermediate component.

7. The joint assembly as described in claim 6, said anchored components each further comprising a widened uneven surface for supporting a corresponding uneven profile associated with said intermediate positioned roller shaped component.

8. The joint assembly as described in claim 6, further comprising a plurality of ball bearings seated in distributed fashion along said concave surface of at least one of said anchored implants for providing rotational support to said roller shaped intermediate component.

9. A multi-component elbow joint assembly incorporated into reconditioned end surfaces established between an upper humerus bone and opposing lower radius and ulna bones, said assembly comprising:
- a first component anchored into the upper humerus reconditioned end surface and exhibiting a first support surface;
- a second component anchored into the lower reconditioned bone end surface of at least one of the radius and ulna bones and exhibiting a second exposed support surface;
- an elongated and uneven roller shaped intermediate component supported in rotational fashion between said first and second anchored components; and
- each of said anchored components further exhibiting a concave surface for supporting therebetween said intermediate component, a plurality of ball bearings seated in distributed fashion along said concave surface of at least one of said anchored implants for providing rotational support to said roller shaped intermediate component.

10. The joint assembly as described in claim 9, said anchored components each further comprising a widened uneven surface for supporting a corresponding uneven profile associated with said intermediate positioned roller shaped component.

11. The joint assembly as described in claim 9, each of said first, second and intermediate components further being constructed of at least one of a metal, plastic, polymer or composite material.

12. The joint assembly as described in claim 9, further comprising a central aperture extending longitudinally through an interior of said uneven roller shaped intermediate component which is engaged by a pin shaft upon pre-positioning said intermediate component between a pair of downward extending end lobes associated with said first component, a first of said end lobes including an inner aperture for permitting initial insertion of said shaft, with an opposite end located and other of said lobes exhibiting an abutting inner end face defining an end stop of said inserting shaft, thereby mounting said roller in a stationary rotatable position.

13. The joint assembly as described in claim 12, further comprising a plurality of micro sized ball bearings seated in distributed fashion along an end face of said first component in substantially embedded and eccentrically rotatable fashion within a concave/irregular support face of said first component, said bearings providing additional rotational support to said intermediate positioned roller.

14. A multi-component elbow joint assembly incorporated into reconditioned end surfaces established between an upper humerus bone and opposing lower radius and ulna bones, said assembly comprising:
- a first component anchored into the upper humerus reconditioned end surface and exhibiting a first support surface;
- a second component anchored into the lower reconditioned bone end surface of at least one of the radius and ulna bones and exhibiting a second exposed support surface;
- an elongated and uneven roller shaped intermediate component supported in rotational fashion between said first and second anchored components;
- a central aperture extending longitudinally through an interior of said uneven roller shaped intermediate component which is engaged by a pin shaft upon pre-positioning said intermediate component between a pair of downward extending end lobes associated with said first component, a first of said end lobes including an inner aperture for permitting initial insertion of said shaft, with an opposite end located and other of said lobes exhibiting an abutting inner end face defining an end stop of said inserting shaft, thereby mounting said roller in a stationary rotatable position; and
- a plurality of micro sized ball bearings seated in distributed fashion along an end face of said first component in substantially embedded and eccentrically rotatable fashion within a concave/irregular support face of said first component, said bearings providing additional rotational support to said intermediate positioned roller.

15. The joint assembly as described in claim 14, each of said first, second and intermediate components further being constructed of at least one of a metal, plastic, polymer or composite material.

* * * * *